United States Patent [19]

Broussard

[11] Patent Number: 5,210,337
[45] Date of Patent: May 11, 1993

[54] FORMALDEHYDE RESISTANT CATALYST FOR HYDROGENATION AND HYDROGENOLYSIS OF ALDEHYDES, ACETALS, AND ESTERS

[75] Inventor: Jerry A. Broussard, Summit, N.J.
[73] Assignee: Hoechst Celanese Corporation, Somerville, N.J.
[21] Appl. No.: 500,103
[22] Filed: Mar. 28, 1990

Related U.S. Application Data

[63] Continuation of Ser. No. 284,609, Dec. 15, 1988, abandoned.
[51] Int. Cl.$^5$ .................. C07C 29/141; C07C 29/149; C07C 29/132; C07C 31/08
[52] U.S. Cl. .................... 568/881; 568/853; 568/862; 568/864; 568/865; 568/885; 568/907
[58] Field of Search ................ 568/853, 862, 864, 865, 568/881, 885, 907

[56] References Cited

U.S. PATENT DOCUMENTS

| | | | |
|---|---|---|---|
| 2,776,318 | 1/1957 | Willke et al. | 568/907 |
| 3,170,958 | 2/1965 | Howard | 568/907 |
| 3,928,459 | 12/1975 | Mercier | 568/907 |
| 4,048,110 | 9/1977 | Vanderspurt | 252/443 |
| 4,104,478 | 8/1978 | Trivedi | 568/885 |
| 4,410,460 | 10/1983 | Qualeatti et al. | 260/409 |
| 4,659,686 | 4/1987 | Griffiths et al. | 502/183 |
| 4,885,410 | 12/1987 | De Thomas | 568/881 |
| 4,985,522 | 1/1991 | Kitson et al. | 568/885 |

FOREIGN PATENT DOCUMENTS 708742   5/1954   United Kingdom ................ 568/907

OTHER PUBLICATIONS

Annals of the New York Academy of Sciences, vol. 145, art. 1, 18 Oct. 1967, pp. 58–71; H. Smith Broadbent: "Rhenium and Its Compounds as Hydrogenation Catalysts".
Cason, "Essential Principles of Organic Chemistry", 1956, pp. 160 and 161.
The Merck Index, eighth ed., 1968, p. 680.
"Rhenium and Its Compounds as Hydrogenation Catalysts, III. Rhenium Heptoxide", H. Smith Broadbent et al., J. Org. Chem., 24, pp. 1847–1854, 1959.
"Rhenium Catalysts. IV. Rhenium (III) Oxide from Perrhenate via Borohydride Reduction", H. Smith Broadbent et al., J. Org. Chem., 27, pp. 4400–4402, 1962.
"Rhenium Catalysts. V. Rhenium Heptoxide-Tetrahydropyran Complex", H. Smith Broadbent et al., J. Org. Chem., 27, pp. 4402–4404, 1962.
"Rhenium Catalysts. VI. Rhenium (IV) Oxide Hydrate", H. Smith Broadbent et al., J. Org. Chem., 28, pp. 2343–2345, 1963.
"Rhenium Catalysts. VII. Rhenium (VI) Oxide", H. Smith Broadbent et al., J. Org. Chem., 28, pp. 2345–2347, 1963.
"Rhenium Catalysts. VIII. Rhenium (II) Oxide Dihydrate from Perrhenate via Alkali Metal-Amine Reductions", H. Smith Broadbent et al., J. Org. Chem., 28, pp. 2347–2350, 1963.

*Primary Examiner*—Joseph E. Evans
*Attorney, Agent, or Firm*—Depaoli & O'Brien

[57] ABSTRACT

Rhenium has been found to be formaldehyde resistant catalyst and is thus useful in the catalytic hydrogenation of carbonyls, acetals and esters to alcohols when the reaction medium contains formaldehyde as a reactant or impurity. Also, rhenium is a useful catalyst in the hydrogenolysis of acylic acetals to alcohols.

11 Claims, No Drawings

FORMALDEHYDE RESISTANT CATALYST FOR HYDROGENATION AND HYDROGENOLYSIS OF ALDEHYDES, ACETALS, AND ESTERS

This application is a continuation of application Ser. No. 284,609, filed Dec. 15, 1988, now abandoned.

FIELD OF THE INVENTION

The present invention is directed to processes for the hydrogenation and hydrogenolysis of aldehydes, acetals, and esters utilizing a formaldehyde-resistant hydrogenation catalyst.

The catalytic hydrogenation of esters and aldehydes is useful in the formation of alcohols, glycols, and polyols. A useful reaction scheme for producing such alcohols involves an aldol condensation with formaldehyde and subsequent hydrogenation of carbonyl groups to the alcohol. Unfortunately, the presence of reactant formaldehyde impurities during the catalytic hydrogenation of the aldol condensation product is disadvantageous as the formaldehyde acts as a catalyst poison adversely affecting hydrogenation. Formaldehyde is also frequently found at low levels in a variety of chemical process streams. Removal of formaldehyde by distillation is often made difficult by the complex, non-ideal volatility behavior of formaldehyde, particularly in the presence of water and alcohols. A combination of catalytic hydrogenation to convert formaldehyde to methanol and subsequent removal of methanol by distillation is potentially easier and more effective. However this approach is precluded by the lack of catalysts for converting formaldehyde to methanol, again because of the known tendency of formaldehyde to poison hydrogenation catalysts. It is believed that the poisoning mechanism resulting from the presence of formaldehyde involves the dehydrogenation of formaldehyde to carbon monoxide which is more strongly chemisorbed on the catalyst than hydrogen.

While many hydrogenation catalysts exist, many of these are known to be poisoned by even minute amounts of formaldehyde and, thus, have at best limited use in the catalytic hydrogenation of aldehydes, esters or acetals in which reactant streams contain positive amounts of unreacted or by-product formaldehyde impurities.

It is known that rhenium oxide will catalyze the hydrogenation of a wide range of substrates. A series of published articles were authored by H. S. Broadbent and coworkers in the 1960's dealing with the use of rhenium "blacks" as hydrogenation catalysts. These rhenium "blacks" were prepared by reduction of $Re_2O_7$ to form lower Re oxides. These Re oxides were effective for reducing a wide range of functional groups including aldehydes, ketones, olefins, acids, esters and amides. See, for example, J. Org. Chem., 24, 1847–54, 1969; J. Org. Chem, 27, 4400–4404, 1962; J. Org. Chem., 28 2343–2350, 1963; and *Annuals of the New York Academy of Sciences*, 145, 58–61, 1967.

The inventor, however, is unaware of any knowledge in the art, including that listed above, relative to the extent of formaldehyde resistance inherent in rhenium hydrogenation catalysts.

A primary objective of the present invention is to provide a formaldehyde-resistant hydrogenation catalyst for the reduction of organic feeds.

A further objective of the present invention is to provide a formaldehyde-resistant hydrogenation catalyst for the reduction of carbonyls, acetals and esters.

SUMMARY OF THE INVENTION

It has now been found that rhenium is a useful hydrogenation catalyst for reducing carbonyls, carboxylic acid esters, acetals and the like even when formaldehyde is present in the reaction medium from the feedstream or formed during the course of the reaction. It has been discovered that the rhenium hydrogenation catalyst maintains hydrogenation activity in the presence of formaldehyde and is, thus, formaldehyde resistant. Although in certain respects, the rhenium catalyst is not as active as other known hydrogenation catalysts, the rhenium catalyst is more formaldehyde resistant than other known catalysts which lose a substantial amount of catalytic activity when formaldehyde is present. In its broadest aspect, the present invention is based on the discovery that rhenium is formaldehyde resistant and can be used to catalyze the hydrogenation of any organic feed for which rhenium is an effective hydrogenation catalyst even in the presence of formaldehyde.

DETAILED DESCRIPTION OF THE INVENTION

The formaldehyde-resistant hydrogenation catalyst for use in this invention comprises a compound of rhenium or metallic rhenium. Preferably, the rhenium catalyst is a rhenium oxide such as $Re_2O_7$ which has been reduced and which comprises a mixture of rhenium oxides. The reduced rhenium oxide catalyst is commercially available as rhenium black such as from Engelhard Corporation. Although not necessary, it is preferred that the rhenium compound be provided on a solid support. Useful supports include high surface area inorganic oxides such as alumina or mixtures of inorganic oxides such as alumina-silica, silica-zirconia, silica-magnesia, etc. A most useful and the preferred support is carbon. If the rhenium is supported, the amount of rhenium present as Re should range from about 0.2 to 5.0 wt.% of the catalyst composite.

The rhenium catalyst is useful in a variety of hydrogenation reactions including the reduction of carbonyls, carboxylic acids and esters and acetals to alcohols, and, in particular, when formaldehyde is present in the feedstreams and/or is formed during the reaction. Any known organic feed which is effectively hydrogenated in the presence of rhenium can still be effectively hydrogenated although formaldehyde is present in the reaction medium. The rhenium catalyst has been found to be surprisingly formaldehyde-resistant and maintains catalytic activity. It is known that levels of formaldehyde as low as 0.1 wt.% can often poison a hydrogenation catalyst. It has been found that the rhenium catalyst is formaldehyde resistant at such low levels up to even about 10 wt.% formaldehyde.

The rhenium catalyst has use in a variety of hydrogenation reactions. It is not intended that the present invention be limited to any of the specific examples of hydrogenation reactions that may be disclosed. It is to be understood that any catalytic hydrogenation can be performed with the rhenium catalyst. The scope of the invention is not to be limited to the particular material being reduced but to the reduction of any material with rhenium where formaldehyde, regardless of source is present in the reaction medium.

Thus, listed below are non-limiting examples of the types of compounds which can be catalytically hydrogenated in the presence of the rhenium catalyst of this invention. Other compounds which can be hydrogenated are disclosed in the published articles authored by H. S. Broadbent et al as discussed above, all of which publications are herein incorporated by reference.

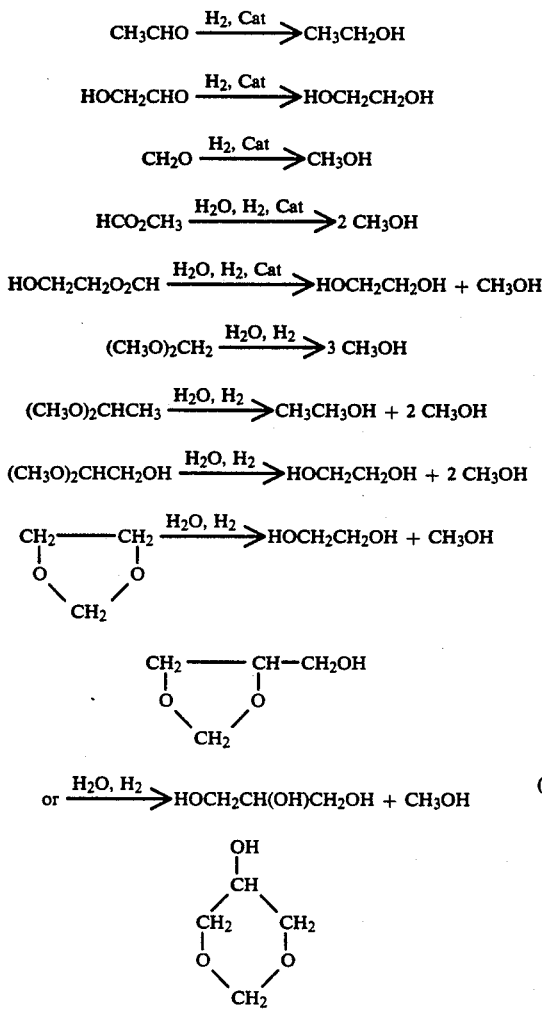

While some of the conversions as listed above are straightforward, most are not, and, thus, the effectiveness of the rhenium catalyst especially when formaldehyde is present is surprising and quite useful. Catalytic hydrogenation of acetaldehyde (1) is a simple, well-established procedure. However, the catalytic hydrogenation of glycolaldehyde (2) is problematic because the molecule tends to "unzip" to form $CH_2O$ with resultant catalyst poisoning. Likewise, the catalytic hydrogenation of formaldehyde (3) is not generally workable with most common catalysts because $CH_2O$ poisons the catalyst. As beforesaid, the probable poisoning mechanism is dehydrogenation of $CH_2O$ to form carbon monoxide (CO) which is more strongly chemisorbed on the catalyst than hydrogen ($H_2$)

Catalytic hydrogenation of esters in general usually proceeds only under forcing conditions (200°–300° C., 1000–5000 psig), and formate esters are more difficult to reduce than most esters (4, 5).

Catalytic hydrogenation of acetals is also a difficult conversion to effect and involves hydrolysis and hydrogenation to yield substantial amounts of product alcohols (6,7,8). In general, a bifunctional catalyst which is acidic to effect hydrolysis and has hydrogenation activity is needed. Commonly observed side reactions lead to the formation of ethers and alkanes, which are surprisingly reduced, if at all present using rhenium as the catalyst.

Cyclic acetals (9,10) with 5-and-6-membered rings are generally more stable than the acyclic counterparts and are correspondingly more difficult to hydrogenate.

The catalyst of the present invention also has use in the formation of polyols such as trimethylolpropane which have been formed by aldol condensations with formaldehyde. Thus, for example, in the first step of the process to make trimethylolpropane, butyraldehyde and formaldehyde are reacted to form an intermediate dimethylol butyraldehyde. The dimethylol butyraldehyde can then be hydrogenated in the presence of the rhenium catalyst to trimethylol propane. The reaction scheme can be expressed as follows:

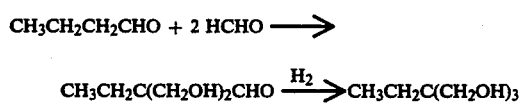

It can be readily seen that various polyols can be formed by an analagous process. Thus, neopentyl glycol can be formed by the catalytic hydrogenation of isobutyraldehyde, etc.

The following examples attempt to illustrate the catalytic activity of a rhenium catalyst and compare such activity when formaldehyde is present in the reaction system as well as compare the formaldehyde resistance of the rhenium catalyst with other known hydrogenation catalysts.

EXAMPLES

A series of commercially available hydrogenation catalysts were tested in a stirred autoclave for catalytic activity under batch conditions. Model compounds were used for the studies. After reaction the liquid products were analyzed by GC to determine if the reactants had been converted, if the expected products had been formed, and if any by-products had been formed. All amounts are by weight percent if not otherwise indicated.

The reaction charges were chosen to show the ability of the catalysts to convert various functional groups alone and in combination. The model compounds employed included the following: acetaldehyde (AcH), formaldehyde ($CH_2O$), glycolaldehyde (GAL), methylal (MeAl), ethyl formal (EtAl), propyl formal (PrAl), dioxolane (DiOX), glycerine formals (GLY-Fo), methyl formate (MeFo), ethyl formate (EtFo) and formic acid (HFo). Solvents for this study include methanol (MeOH), ethanol (EtOH), n-propanol (PrOH), ethylene glycol (EG), and water.

The catalysts evaluated in this study included rhenium on carbon (Re/C), ruthenium on carbon (Ru/C), rhodium on carbon (Rh/C), palladium on carbon (Pd/C), chromium-promoted Raney nickel (RaNi), Raney copper (RaCu), copper chromite ($CuCrO_2$), nickel on kieslguhr (Ni/Kies) and cobalt on kieselguhr (Co/kies).

EXAMPLE 1

Rhenium on Carbon

Rhenium on carbon (Re/C) was evaluated as a hydrogenation catalyst. The catalyst employed was obtained from Engelhard and contained 0.5% Re as Re₂O₇ reduced and supported on granular carbon. Experimental hydrogenation conditions most commonly employed were 4 wt% catalyst and 2.0 hours of reaction time. Reaction temperatures in the range of 100°–210° C. and pressures up to 2000 psig were examined. Results are presented in Tables 1–3.

the complexity of this product mixture, it was not possible to establish the yields of reduced products from each starting material.

TABLE 1

Catalytic Reduction of Aldehydes with Rhenium on Carbon

| Sample No. | | MeOH | EtOH | H₂O | AcH | CH₂O | Others | Others | Others | Temp °C. | P, Psig |
|---|---|---|---|---|---|---|---|---|---|---|---|
| 1 | feed | 80.0 | — | 10.0 | 10.0 | — | — | — | — | 165 | 1500 |
|   | product | 79.9 | 9.1 | 14.4 | ND* | — | — | — | — |   |   |
| 2 | feed | 74.0 | — | 10.0 | 10.0 | — | MeAl 5.0 | MeFo 1.0 | — | 165 | 1500 |
|   | product | 79.6 | 9.6 | 14.4 | 0.4 | — | MeAl 4.8 | MeFo Present | Uknown/0.1 EtFo/0.1 |   |   |
| 3 | feed | 80.0 | — | 10.0 | 10.0 | — | — | — | — | 100 | 1500 |
|   | product | 92.2 | 6.1 | 17.0 | 2.9 | — | — | — | — |   |   |
| 4 | feed | — | 85.0 | 10.0 | — | 5.0 | — | — | — | 105 | 1500 |
|   | product | 1.1 | 82.2 | 11.3 | — | 3.4 | EtAl 2.5 | — | — |   |   |
| 5 | feed | — | 85.0 | 10.0 | — | 5.0 | — | — | — | 165 | 1500 |
|   | product | 3.9 | 72.9 | 15.2 | — | ND | EtAl 6.2 | — | — |   |   |
| 6 | feed | — | 50.0 | 30.0 | 5.0 | 5.0 | ETAl 5.0 | EtFo 5.0 | — | 200 | 1500 |
|   | product | 5.9 | 60.1 | 30.8 | 0.2 | ND | EtAl 1.2 | EtFo 0.8 | Acetaldol 0.3 |   |   |
| 7 | feed | — | 50.0 | 30.0 | 5.0 | 5.0 | EtAl 5.0 | EtFo 5.0 | — | 200 | 1500 |
|   | product | 6.2 | 61.2 | 29.9 | ND | ND | EtAl 0.3 | EtFo 0.7 | Acetaldol 0.3 |   |   |
| 8 | feed | — | 50.0 | 30.0 | 5.0 | 5.0 | EtAl 5.0 | EtFo 5.0 | — | 200 | 1500 |
|   | product | 6.3 | 59.6 | 28.7 | ND | ND | EtAl ND | EtFo 0.7 | Acetaldol 0.7 |   |   |
| 9 | feed | — | 50.0 | 30.0 | 5.0 | 5.0 | EtAl 5.0 | EtFo 5.0 | — | 200 | 1500 |
|   | product | 6.3 | 60.1 | — | 0.1 | ND | EtAl ND | EtFo 0.7 | Acetaldol 1.4 |   |   |

*Not detected

Aldehydes

Table I sets forth the results of hydrogenation of various aldehydes with the Re/C catalyst.

Acetaldehyde (AcH) was used as a model for simple aldehydes in this example. Results indicated that Re/C was an effective but not extremely active catalyst for reducing AcH to ethanol. Complete conversion was achieved at 165° C. after 2 hours (Sample 1) but not at 100° C. (Sample 3). Neither methyl formate nor methylal had a large effect on AcH reduction (Sample 2).

CH₂O was reduced to methanol by Re/C. At 105° C. for 2 hours, the conversion of CH₂O to methanol was low (ca. 20%) (Sample 4). However, at 165° C., CH₂O conversion was complete (Sample 5) with about 80% of the CH₂O being reduced to methanol and the remainder being converted to formals.

A series of four hydrogenation experiments (Samples 6–9) were conducted at 200° C. reusing the same catalyst charge for each successive batch. The reaction charge contained a mixture of acetaldehyde, formaldehyde, ethyl formal, and ethyl formate in aqueous ethanol. Even at the high CH₂O level employed (5%), AcH conversion was complete with little or no acetaldol formation. Acetaldol is the aldol condensation product of AcH itself. It was observed that if AcH was not quickly reduced, much of it was converted to the aldol product. Moreover, the catalyst activity did not decrease over the course of these five catalyst reuse cycles. CH₂O conversion was essentially complete for all five reactions. EtFo and EtAl conversions were both in the range of 80–100% for all experiments. Because of Formals Propyl formal (PrAl) was used as a model for acyclic formals in most of the experiments, see Table 2. At 160° C. in the absence of added acid, PrAl in ethylene glycol (EG) solution was completely consumed with substantial yield of methanol plus some accompanying transacetalization (Samples 1 and 2). When the experiment was repeated in n-propanol, an 84.5% yield of methanol was obtained based on the amount of PrAl converted. No products other than n-propanol and methanol were detected (Sample 3). At 206° C. in ethylene glycol solvent, conversion of PrAl is essentially complete with only low levels of competing transacetalization (Sample 4). Attempts to hydrogenate methylal (MeAl) at 165° C. (Samples 5,6 and 7) lead to results similar to those obtained with PrAl.

The effects of added acids on the hydrogenation of PrAl were also examined. At 100° C. in ethylene glycol solvent and in the presence of 4% Amberlyst 15 (sulfonic acid ion exchange resin produced by Rohm and Haas), complete conversion of PrAl was achieved. However, the yield of methanol is well below the expected level, indicating that PrAl had mainly undergone transacetalization rather than hydrogenation (Sample 8). At 120° C. in n-propanol solution with 2% Amberlyst 15, about 65% conversion was achieved with a corresponding yield of methanol (Sample 9). Under these conditions, transacetalization does not obscure the hydrogenation results.

Two soluble acids were also examined as cocatalysts for Re/C in the hydrogenation of PrAl. Phosphoric acid (H₃PO₄) facilitates the hydrogenation of PrAl at 165° C. (Sample 10). Boric acid ($H_3BO_3$) has no effect on the process (Sample 11).

Attempts were made to hydrogenate two cyclic acetals (formals), e.g. dioxolane (DIOX) and the isomeric pair of glycerine formals (GLY-Fo), with Re/C at 165° C. About 15% of the DIOX is hydrolyzed to ethylene glycol and the liberated $CH_2O$ reduced to methanol (Sample 12). In contrast, GLY-FO did not undergo appreciable reduction at either 165° C. (Sample 13) or at 200° C. (Sample 14).

Three acids were used in conjunction with Re/C to try to improve the hydrogenation of DIOX. Amberlyst 15 at 105° C. (Sample 15) and 123° C. (Sample 16) led to more transacetalization than hydrogenation. $H_3PO_4$ and $H_3BO_3$ were also evaluated as hydrolysis promoters in conjunction with Re/C. $H_3PO_4$ increases the rate of DIOX conversion. However, no methanol product is observed (Samples 17, 18). The significance of no methanol production was not clear.

TABLE 2

Catalytic Reduction of Formals with Rhenium on Carbon

| Sample No. | | MeOH | EtOH | H$_2$O | MeAl | EG | Others | Others | Others | Temp °C. | P, Psig |
|---|---|---|---|---|---|---|---|---|---|---|---|
| 1 | feed | — | — | 30.0 | — | 60.0 | PrAl 10.0 | — | — | 160 | 1500 |
| | product | 2.2 | — | 31.7 | — | 72.5 | PrAl ND | n-PrOH 5.8 | Diox 0.3 | | |
| 2 | feed | — | — | 30.0 | — | 60.0 | PrAl 10.0 | — | — | 165 | 1500 |
| | product | 0.5 | — | 29.5 | — | 70.5 | PrAl 0.5 | n-PrOH 7.2 | Diox 0.1 | | |
| 3 | feed | — | — | 30.0 | — | — | PrAl 10.0 | n-PrOH 60.0 | — | 165 | 1500 |
| | product | 1.4 | — | 30.3 | — | — | PrAl 3.1 | n-PrOH 65.7 | | | |
| 4 | feed | — | — | 30.0 | — | 60.0 | PrAl 10.0 | — | — | 206 | 1500 |
| | product | 1.8 | 1.3 | 33.9 | Present | | PrAl ND | PrOH Present | Diox 0.4 | | |
| 5 | feed | — | 80.0 | 10.0 | 10.0 | — | — | — | — | 165 | 1500 |
| | product | 1.4 | 81.7 | 11.0 | 6.7 | — | MeEt Formal 1.3 | EtAl 0.5 | | | |
| 6 | feed | — | 60.0 | 30.0 | 10.0 | — | — | — | — | 165 | 1500 |
| | product | 2.0 | 57.8 | 27.9 | 6.8 | — | MeEt Formal 0.8 | EtAl 0.2 | | | |
| 7 | feed | — | — | 30.0 | 10.0 | 60.0 | — | — | — | 165 | 1500 |
| | product | 5.3 | 0.2 | 28.2 | 1.8 | 55.9 | — | — | — | | |
| 8 | feed | — | — | 30.0 | — | 60.0 | PrAl 10.0 | — | A-15 4.0 | 100 | 1500 |
| | product | 0.3 | — | 34.4 | — | 64.5 | PrAl ND | n-PrOH 4.3 | Diox 0.3 | | |
| 9 | feed | — | — | 30.0 | — | — | PrAl 10.0 | PrOH 60.0 | A-15 2.0 | 120 | 1500 |
| | product | 0.9 | — | 31.1 | — | — | PrAl 3.5 | PrOH 64.0 | | | |
| 10 | feed | — | — | 30.0 | — | — | PrAl 10.0 | PrOH 60.0 | H$_3$PO$_4$ 0.4 | 165 | 1500 |
| | product | 2.1 | — | 30.1 | | | PrAl 0.5 | PrOH 67.0 | — | | |
| 11 | feed | — | — | 30.0 | — | — | PrAl 10.0 | PrOH 60.0 | H$_3$BO$_3$ 2.0 | 160 | 1500 |
| | product | 1.1 | — | 30.7 | — | — | PrAl 4.1 | PrOH 63.9 | | | |
| 12 | feed | — | 60.0 | 30.0 | — | — | Diox 10.0 | — | — | 205 | 1500 |
| | product | 0.6 | 65.4 | 32.3 | — | 0.2 | Diox 8.6 | — | — | | |
| 13 | feed | — | 65.0 | 30.0 | — | — | Gly—Fo 5.0 | — | — | 165 | 1500 |
| | product | 0.1 | 67.1 | 32.2 | — | — | Gly—Fo 5.1 | EtAl ND | | | |
| 14 | feed | — | 65.0 | 30.0 | — | — | Gly—Fo 5.0 | — | — | 200 | 1500 |
| | product | 0.1 | 64.3 | 31.6 | — | | Gly—Fo 5.0 | — | — | | |
| 15 | feed | — | 60.0 | 30.0 | — | — | Diox 10.0 | A-15 4.0 | — | 105 | 1500 |
| | product | 0.8 | 51.9 | 29.6 | — | 12.1 | Diox 0.5 | EtAl 6.6 | | | |
| 16 | feed | — | — | 30.0 | — | 60.0 | Diox 10.0 | A-15 4.0 | | 123 | 1500 |
| | product | ND | — | 29.6 | — | 65.6 | Diox 3.7 | Uknown 0.9 | — | | |
| 17 | feed | — | — | 30.0 | — | 60.0 | Diox 10.0 | H$_3$PO$_4$ 0.2 | | 162 | 1800 |
| | product | ND | — | 29.3 | — | 66.5 | Diox 2.1 | Unknown 2.1 | | | |

TABLE 2-continued

Catalytic Reduction of Formals with Rhenium on Carbon

| Sample No. | MeOH | EtOH | H$_2$O | MeAl | EG | Others | Others | Others | Temp °C. | P, Psig |
|---|---|---|---|---|---|---|---|---|---|---|
| 18 feed | — | — | 30.0 | — | 60.0 | Diox 10.0 | H$_3$BO$_3$ 1.0 | | 165 | 1800 |
| product | ND | — | 33.8 | — | 59.0 | Diox 5.5 | | | | |

Formates

At 160° C. in ethylene glycol solvent, about 85% of the ethyl formate (EtFo) is converted, see Table 3 (Sample 1). Whether formate was transesterified or decomposed to alcohol and CO was not clear. However, no methanol was detected in the product. At 210° C. in ethanol solvent, 80% of the EtFo was converted (Sample 2). Under these conditions transesterification was not a factor, but still no methanol was detected. Apparently the EtFo was decomposed to ethanol and CO.

TABLE 3

Catalytic Reduction of Formates with Rhenium on Carbon

| Sample No. | MeOH | EtOH | H$_2$O | EG | Others | Others | Temp °C. | P, Psig |
|---|---|---|---|---|---|---|---|---|
| 1 feed | — | — | 30.0 | 60.0 | EtFo 10.0 | | 160 | 1500 |
| product | ND | 5.7 | 34.3 | 71.5 | EtFo | Unknown 1.3 | 0.8 | |
| 2 feed | — | 60.0 | 30.0 | — | EtFo 10.0 | — | 210 | 1500 |
| product | 0.1 | 67.5 | 32.8 | — | EtFo | — 2.2 | | |

Re/C is a good hydrogenation catalyst, although it is relatively inactive and requires high reaction temperatures. However, it effectively reduces AcH and CH$_2$O, and the AcH reduction is not seriously poisoned by CH$_2$O. In addition, the cumulative effects of CH$_2$O poisoning are minor.

Re/C is also an effective catalyst for decomposing formates in the range of 160°-210° C. Because no by-product methanol was found when EtFo was treated with Re/C and H$_2$ it is believed that formates are decomposed to alcohols and CO rather than hydrogenated.

Re/C is also an effective catalyst for hydrolysis/reduction of acyclic formals in the temperature range of 160°-210° C. Unfortunately it is less effective with cyclic acetals. Although dioxolane is partially reduced by Re/C, glycerine formals, are essentially not reduced by H$_2$ and Re/C at 165°-200° C. The use of acids in conjunction with Re/C slightly improved the rate of cyclic formal hydrolysis.

EXAMPLE 2

Ruthenium on Carbon

Ruthenium on carbon (Ru/C) was also examined as a hydrogenation catalyst, in particular, for the effect formaldehyde may have on the activity of the catalyst. The material used was obtained from Matthey Bishop and contained 5% Ru on granular carbon. Experimental results are described in Table 4. Typical reaction conditions employed were the following: 4 wt% catalyst, 100° C., 1000 psig, and 2.0 hours reaction time. Temperatures up to 200° C. and pressures up to 1500 psig were also examined.

Aldehydes

Acetaldehyde (AcH) was completely converted to ethanol plus a small amount of acetaldol under standard conditions (Sample 1). The conversion of AcH was not greatly affected by the presence of MeAl or MeFo (Sample 2) or low levels (0.5%) of CH$_2$O (Sample 3). However, 4% CH$_2$O (Sample 4) completely suppressed ethanol formation, and extensive conversion of AcH to by-products including acetaldol occurred. In low concentration (0.5%), CH$_2$O was reduced to methanol.

The effect of reusing a catalyst sample through several cycles of AcH reduction in the presence of 0.5% CH$_2$O was also examined (Samples 5-9). The level of AcH conversion did not change greatly over five cycles. However, with each additional cycle, more of the AcH underwent aldol condensation and less was reduced to ethanol. Clearly, there was a cumulative catalyst poisoning effect resulting from the repeated exposure to CH$_2$O.

As reported in the literature, Ru/C is a good hydrogenation catalyst for aliphatic aldehydes. On a single pass basis, it was resistant to poisoning by low levels of CH$_2$O. However, it was poisoned by higher levels of CH$_2$O and by repeated exposure to low levels of CH$_2$O (cumulative CH$_2$O poisoning).

TABLE 4

Catalytic Reduction With Ruthenium on Carbon

| Sample No. | MeOH | EtOH | H$_2$O | AcH | MeAl | MeFo | CH$_2$O | Acetaldol | Other | Temp °C. | P, Psig |
|---|---|---|---|---|---|---|---|---|---|---|---|
| 1 feed | 80.0 | — | 10.0 | 10.0 | — | — | — | — | | 100 | 1000 |
| product | 73.8 | 8.7 | 12.6 | ND | — | — | — | 0.3 | | | |
| 2 feed | 74.0 | — | 10.0 | 10.0 | 5.0 | 1.0 | — | — | | 100 | 1000 |
| product | 69.7 | 8.2 | 13.2 | 0.2 | 1.3 | ND | 0.2 | 0.2 | | | |
| 3 feed | 73.5 | — | 10.0 | 10.0 | 5.0 | 1.0 | 0.5 | — | | 104 | 1000 |
| product | 73.2 | 9.3 | 12.4 | 0.1 | 3.2 | 0.2 | ND | — | | | |

TABLE 4-continued

Catalytic Reduction With Ruthenium on Carbon

| Sample No. | MeOH | EtOH | H₂O | AcH | MeAl | MeFo | CH₂O | Acetaldol | Other | Temp °C. | P, Psig |
|---|---|---|---|---|---|---|---|---|---|---|---|
| 4 feed | 70.0 | — | 10.0 | 10.0 | 5.0 | 1.0 | 4.0 | — | | 100 | 1000 |
| product | 72.8 | ND | 14.0 | 4.0 | 3.8 | 0.8 | 3.6 | 0.4 | | | |
| 5 feed (1st | 79.5 | — | 10.0 | 10.0 | — | — | 0.5 | 1.8 | | 103 | 1000 |
| cycle) prod. | 82.3 | 6.6 | 11.1 | 0.6 | — | — | 0.1 | 2.0 | | | |
| 6 (2nd cycle) product | 78.5 | 5.1 | 10.6 | 1.4 | — | — | 0.2 | 4.4 | | 105 | 1000 |
| 7 (3rd cycle) product | 76.8 | 4.5 | 13.8 | 1.6 | 0.2 | — | 0.5 | 5.7 | MeAl | 106 | 1000 0.2 |
| 8 (4th cycle) product | 78.5 | 3.8 | 14.6 | 1.8 | — | — | 0.6 | 6.8 | | 103 | 1000 |
| 9 (5th cycle) product | 75.3 | 3.7 | 13.8 | 1.6 | — | — | 0.6 | 7.8 | | 103 | 1000 |

EXAMPLE 3

Copper Chromite

In this example copper chromite ($CuCrO_2$) was used as the hydrogenation catalyst. The catalyst was obtained from Harshaw Catalyst Co. $CuCrO_2$ is well known as a catalyst for hydrogenation of aldehydes and hydrogenolysis of esters. However, temperatures in the range of 200°–250° C. are usually required in order to obtain acceptable activity. The test conditions employed were 200°–210° C., 1500 psig and 2.0 hours reaction time. Results are presented in Table 5.

$CuCrO_2$ was quite active for hydrogenation of AcH with no detectable acetaldol formation (Sample 1). $CH_2O$ (Sample 3) and paraform (Sample 5) were both converted to methanol under these conditions. There was little evidence of $CH_2O$ poisoning. Glycolaldehyde was converted to ethylene glycol under these process conditions (Sample 7).

MeFo appears to be converted under these conditions. However, subsequent studies with EtFo indicated that although 80–90% of the EtFo was converted, 10% of the theoretical yield of methanol was observed. This suggests that EtFo may be undergoing transesterification or decomposition to ethanol and CO rather than undergoing hydrogenolysis to ethanol and methanol.

MeAl conversion under these conditions was quite low. This is perhaps not surprising because $CuCrO_2$ has little or none of the acidic character needed for the initial hydrolysis.

In summary, $CuCrO_2$ showed good activity for reducing aldehydes and $CH_2O$ and was resistant to $CH_2O$ poisoning. It was not effective for the hydrogenation of formals. It showed some activity for formate ester hydrogenolysis, however, higher temperatures were needed for this conversion. However, $CuCrO_2$ is known to be rapidly deactivated by $H_2O$ and acids.

TABLE 5

Catalytic Reduction With Copper Chromite

| Sample No | MeOH | EtOH | H₂O | AcH | MeAl | MeFo | CH₂O | Acetaldol | GAL | EG | Other | Temp °C. | P, Psig |
|---|---|---|---|---|---|---|---|---|---|---|---|---|---|
| 1 feed | 80 | — | 10 | 10 | — | — | — | — | — | — | — | 200 | 1500 |
| product | — | 12.3 | 12.0 | ND | — | — | — | — | — | — | — | | |
| 2 feed | 74 | — | 10.0 | 10.0 | 5.0 | 1.0 | — | — | — | — | — | 200 | 1500 |
| product | — | 10.1 | 13.7 | 0.2 | 3.5 | ND | ND | — | — | — | — | | |
| 3 feed | 70.0 | — | 10.0 | 10.0 | 5.0 | 1.0 | 4.0 | — | — | — | — | 200 | 1500 |
| product | 71.9 | 9.6 | 13.8 | 0.1 | 3.8 | ND | ND | 0.3 | — | — | — | | |
| 4 feed | 73.5 | — | 10.0 | 10.0 | 5.0 | 1.0 | 0.5 | — | — | — | — | 200 | 1500 |
| product | 73.2 | 9.7 | 13.5 | 0.1 | 3.4 | ND | ND | 0.3 | — | — | — | | |
| 5 feed | — | — | 1.0 | — | — | — | 5.0 | — | — | 94.0 | — | 210 | 1500 |
| product | 3.9 | — | 5.8 | — | — | Paraform ND | — | — | — | 89.5 | Diox 0.5 | | |
| 6 feed | — | — | 1.0 | — | — | — | — | — | — | 89.0 | EtFo 10.0 | 210 | 1500 |
| product | 0.3 | 4.2 | 2.6 | — | — | — | — | — | — | 91.5 | EtFo 1.5 | | |
| 7 feed | — | 98.0 | 1.0 | — | — | — | — | — | 1.0 | — | — | 210 | 1500 |
| product | — | 98.4 | 3.3 | — | — | — | — | — | ND | 0.9 | — | | |

EXAMPLE 4

Palladium on Carbon

The palladium catalyst employed in this example contained 5% Pd on carbon (Pd/C) and was obtained from Engelhard Catalyst Company. The test conditions employed were 100° C., 1000 psig, and 2.0 hours reaction time. Results are presented in Table 6.

Palladium has been used as a hydrogenation catalyst for reducing aliphatic aldehydes. However, it tends to hydrogenate aldehydes to alkanes rather than reduce them to alcohols and is more commonly employed for reducing aromatic aldehydes.

Under the above conditions, Pd/C was quite active for hydrogenation of acetaldehyde with no detectable acetaldol formation (Sample 1). Pd/C also exhibited some hydrogenation activity toward MeAl and MeFo. However, it was severely poisoned by $CH_2O$. In the presence of $CH_2O$, AcH conversion was suppressed, and acetaldol formation became a significant side reaction. $CH_2O$ was not hydrogenated to a significant extent under these conditions (Samples 3 and 4).

TABLE 6

Catalytic Reduction With Palladium on Carbon

| Sample No. | | MeOH | EtOH | H₂O | AcH | MeAl | MeFo | CH₂O | Acetaldol | Temp °C. | P, Psig |
|---|---|---|---|---|---|---|---|---|---|---|---|
| 1 | feed | 80.0 | — | 10.0 | 10.0 | — | — | — | — | 100 | 1000 |
|   | product | 77.3 | 10.0 | 12.8 | 0.2 | — | — | — | — | | |
| 2 | feed | 74.0 | — | 10.0 | 10.0 | 5.0 | 10 | — | — | 100 | 1000 |
|   | product | 78.6 | 6.4 | 11.0 | 0.5 | 2.3 | 0.3 | ND | — | | |
| 3 | feed | 70.0 | — | 10.0 | 10.0 | 5.0 | 1.0 | 4.0 | — | 100 | 1000 |
|   | product | 69.0 | 0.7 | 14.0 | 4.0 | 3.8 | 0.5 | 5.7 | 2.4 | | |
| 4 | feed | 73.5 | — | 10.0 | 10.0 | 5.0 | 1.0 | 0.5 | — | 101 | 1000 |
|   | product | 74.4 | 3.5 | 12.4 | 2.2 | 4.2 | 0.5 | 0.3 | 2.1 | | |

EXAMPLE 5

Rhodium on Carbon

The rhodium catalyst employed in this example contained 5% Rh on carbon and was obtained from Matthey Bishop. Test conditions were 100° C., 1000 psig, and 2.0 hours reaction time. Experimental results are presented in Table 7.

Rh/C is known to be an effective catalyst for hydrogenation of aromatic aldehydes.

Rh/C catalyst was fairly active with regard to conversion of AcH. However, about half of the AcH was converted to acetaldol. The rhodium catalyst was not effective for hydrogenation of MeAl and MeFo and was moreover poisoned by CH₂O.

TABLE 7

Catalytic Reduction With Rhodium on Carbon

| Sample No. | | MeOH | EtOH | H₂O | AcH | MeAl | MeFo | CH₂O | Acetaldol | Temp °C. | P, Psig |
|---|---|---|---|---|---|---|---|---|---|---|---|
| 1 | feed | 80.0 | — | 10.0 | 10.0 | — | — | — | — | 106 | 1000 |
|   | product | 77.5 | 5.2 | 13.3 | 0.5 | — | — | — | 3.5 | | |
| 2 | feed | 74.0 | — | 10.0 | 10.0 | 5.0 | 1.0 | — | — | 103 | 1000 |
|   | product | 72.8 | 1.9 | 14.4 | 1.2 | 2.4 | 0.4 | 0.7 | 6.2 | | |
| 3 | feed | 70.0 | — | 10.0 | 10.0 | 5.0 | 1.0 | 4.0 | — | 104 | 1000 |
|   | product | — | 0.7 | 17.3 | 2.1 | 11.1 | 0.5 | 0.6 | 5.6 | | |
| 4 | feed | 73.5 | — | 10.0 | 10.0 | 5.0 | 1.0 | 0.5 | — | 105 | 1000 |
|   | product | 73.5 | 3.4 | 13.0 | 1.4 | 5.1 | 0.6 | 0.2 | 3.0 | | |

EXAMPLE 6

Chromium-Promoted Raney Nickel

The chromium-promoted Raney Nickel (RaNi) (#24, W. R. Grace) was obtained in an activated form under H₂O and was used without further treatment. The test conditions employed were 100° C., 1000 psig, and 2.0 hours of reaction time. Results are presented in Table 8.

RaNi was active for catalytic hydrogenation of AcH, however, a significant amount of acetaldol by-product was formed. Basic materials remaining on the catalyst from the activation procedure are probably responsible for this side reaction. The catalyst was not effective for the hydrogenation of MeAl or MeFo, and it was badly poisoned by CH₂O.

TABLE 8

Catalytic Reduction With Chromium Promoted Raney Nickel

| Sample No. | | MeOH | EtOH | H₂O | AcH | MeAl | MeFo | CH₂O | Acetaldol | Temp °C. | P, Psig |
|---|---|---|---|---|---|---|---|---|---|---|---|
| 1 | feed | 80.0 | — | 10.0 | 10.0 | — | — | — | — | 105 | 1000 |
|   | product | 79.2 | 7.8 | 11.5 | 0.1 | — | — | — | 6.6 | | |
| 2 | feed | 74.0 | — | 10.0 | 10.0 | 5.0 | 1.0 | — | — | 103 | 1000 |
|   | product | 70.0 | 5.6 | 12.8 | 1.9 | 3.9 | 0.5 | ND | 0.7 | | |
| 3 | feed | 70.0 | — | 10.0 | 10.0 | 5.0 | 1.0 | 4.0 | — | 103 | 1000 |
|   | product | 70.1 | 0.7 | 13.0 | 7.8 | 4.1 | 0.7 | 3.7 | 1.3 | | |
| 4 | feed | 73.5 | — | 10.0 | 10.0 | 5.0 | 1.0 | 0.5 | — | 105 | 1000 |
|   | product | 71.8 | 1.3 | 13.6 | 5.9 | 3.6 | 0.5 | 0.5 | 1.3 | | |

EXAMPLE 7

Raney Copper

The Raney copper (RaCu) employed for this example (No. 29, W. R. Grace) was received in the form of an activated water suspension and was used with no further treatment. The catalyst was evaluated at 100° C., 1000 psig, with a two-hour reaction time. Results are presented in Table 9.

It was observed that RaCu exhibits relatively low catalytic activity for hydrogenation of AcH, and that much of the AcH was converted to acetaldol. The catalyst showed very little activity toward MeAl and MeFo and was badly poisoned by CH₂O.

TABLE 9

Catalytic Reduction With Raney Copper

| Sample No. | | MeOH | EtOH | H₂O | AcH | MeAl | MeFo | CH₂O | Acetaldol | Temp °C. | P, Psig |
|---|---|---|---|---|---|---|---|---|---|---|---|
| 1 | feed | 80 | — | 10 | 10.0 | — | — | — | — | 104 | 1000 |
|   | product | 75.0 | 5.6 | 13.7 | 0.8 | — | — | — | 1.0 | | |

TABLE 9-continued

| | Catalytic Reduction With Raney Copper | | | | | | | | | |
|---|---|---|---|---|---|---|---|---|---|---|
| Sample No. | MeOH | EtOH | H$_2$O | AcH | MeAl | MeFo | CH$_2$O | Acetaldol | Temp °C. | P, Psig |
| 2 feed | 74.0 | — | 10.0 | 10.0 | 5.0 | 1.0 | — | — | 102 | 1000 |
| product | 70.2 | 4.0 | 13.6 | 3.1 | 3.7 | 0.5 | ND | 0.6 | | |
| 3 feed | 70.0 | — | 10.0 | 10.0 | 5.0 | 1.0 | 4.0 | — | 105 | 1000 |
| product | 65.4 | 1.3 | 13.5 | 3.7 | 3.9 | 0.6 | 3.2 | 3.2 | | |
| 4 feed | 73.5 | — | 10.0 | 10.0 | 5.0 | 1.0 | 0.5 | — | 105 | 1000 |
| product | 78.1 | 1.7 | 11.4 | 2.0 | 1.9 | 0.2 | 0.4 | 1.1 | | |

EXAMPLE 8

Nickel on Kieselguhr

Nickel on kieselguhr was also examined as a hydrogenation catalyst. The material used (Girdler G49A) was in the form of pellets (3/16"×⅛") and had been reduced and stabilized by the manufacturer. The catalyst contained 58.6 wt% nickel. Test conditions were the following: 4% catalyst, 100° C., 1000 psig, and 2.0 hours reaction time. Results are presented in Table 10. Ni/Kies has been reported as a suitable catalyst for hydrogenation of glycolaldehyde to ethylene glycol. Because glycolaldehyde may decompose to release CH$_2$O under reaction, it was presumed that Ni/Kies might be a CH$_2$O resistant catalyst.

AcH was reduced quantitatively to ethanol under these conditions with no detectable acetaldol by-products (Samples 1 and 5). However, AcH reduction was inhibited by MeAl, MeFo, or CH$_2$O. In the presence of CH$_2$O, substantial amounts of acetaldol were also formed (Samples 3 and 4).

Partial reduction of CH$_2$O to methanol was achieved under these conditions. However, Ni/Kies was almost completely inactive for the hydrogenolysis of EtFo, or the reduction of PrAl and DIOX.

EXAMPLE 9

Cobalt on Kieselguhr

Cobalt on kieselguhr (Co/Kies) was also evaluated as a hydrogenation catalyst. The material used was a promoted Co on kieselguhr obtained from Girdler (G-67) in the form of pellets (3/16"×⅛"). Test conditions employed were the following: 4% catalyst, 100° C., 100–1300 psig, and 2.0 hours of reaction time. Results of these experiments are presented in Table 11.

A series of four experiments was performed in which the same sample of catalyst was used to hydrogenate four successive batches of reactor feed containing acetaldehyde, formaldehyde, ethyl formal, and ethyl formate. The reduction of acetaldehyde was inhibited by the presence of formaldehyde, although formaldehyde was completely coverted. Conversion of ethyl formal, and ethyl formate was low.

In summary, Co/Kies was an unacceptable hydrogenation catalyst. It was inactive to acetals and formals, and it was badly poisoned by formaldehyde.

TABLE 11

| | Catalytic Reduction with Cobalt on Kierelgur | | | | | | | | |
|---|---|---|---|---|---|---|---|---|---|
| Sample No. | MeOH | EtOH | H$_2$O | AcH | CH$_2$O | Etal | EtFo | Temp °C. | P, Psig |
| 1 feed | — | 54.5 | 30.0 | 50.0 | 0.5 | 5.0 | 5.0 | | |
| (1st cycle) product | 0.4 | 56.4 | 34.8 | 2.9 | ND | 3.4 | 2.1 | 103 | 1000 |
| (2nd cycle) product | 0.2 | 55.4 | 33.1 | 3.1 | ND | 4.4 | 4.3 | 105 | 1300 |
| 2 feed | — | 59.5 | 30.0 | 5.0 | 0.5 | 5.0 | | | |
| (3rd cycle) product | 0.2 | 61.6 | 30.4 | 2.6 | ND | 5.1 | — | 105 | 1300 |
| (4th cycle) product | 0.1 | 62.1 | 29.0 | 3.6 | ND | 4.7 | — | 101 | 1300 |

What is claimed is:

1. In a process for catalytically hydrogenating an organic feed in a reaction medium which includes formaldehyde or formaldehyde precursors which are converted to formaldehyde during reaction, the improve-

TABLE 10

| | Catalytic Reduction With Nickel on Kieselguhr | | | | | | | | | | |
|---|---|---|---|---|---|---|---|---|---|---|---|
| Sample No. | MeOH | EtOH | H$_2$O | AcH | MeAl | MeFo | CH$_2$O | Others | Others | Temp °C. | P, Psig |
| 1 feed | 80.0 | — | 10.0 | 10.0 | — | — | — | — | — | 105 | 1000 |
| product | 81.2 | 8.3 | 10.6 | ND | — | — | — | — | — | | |
| 2 feed | 74.0 | — | 10.0 | 10.0 | 5.0 | 1.0 | — | — | — | 103 | 1000 |
| product | 78.3 | 4.1 | 12.1 | 2.2 | 3.3 | ND | — | — | — | | |
| 3 feed | 79.5 | — | 10.0 | 10.0 | — | — | 0.5 | — | — | 103 | 1000 |
| product | 76.0 | 6.5 | 10.9 | 0.3 | — | — | 0.1 | Acetaldol 3.7 | EtFo 6.5 | | |
| 4 feed | 76.0 | — | 10.0 | 10.0 | — | — | 4.0 | — | — | 103 | 1000 |
| product | 76.0 | 3.9 | 12.5 | 1.7 | — | — | ND | Acetaldol 10.0 | — | | |
| 5 feed | 80.0 | — | 10.0 | 10.0 | | | | | | 103 | 1000 |
| product | 80.3 | 9.0 | 10.5 | ND | — | — | — | — | — | | | ment comprising: said organic feed being selected from the group consisting of an acetal, an ester and acetaldehyde and hydrogenating said organic feed in the presence of a catalyst comprising rhenium oxide or mixture of rhenium oxides.

2. The process of claim 1 wherein said rhenium catalyst is provided on an inert support.

3. The process of claim 2 wherein said inert support is carbon.

4. The process of claim 1 wherein said feed comprises an acetal.

5. The process of claim 4 wherein said acetal is an acyclic acetal.

6. The process of claim 1 wherein said feed comprises an ester.

7. The process of claim 5 wherein said feed includes water.

8. The process of claim 6 wherein said ester is a formate ester and said feed further includes water.

9. The process of claim 1 wherein the formaldehyde is present in the reaction medium in an amount from about 0.1 to 5 wt%.

10. The process of claim 1 wherein said feed is acetaldehyde.

11. The process of claim 4 wherein said acetal is a cyclic acetal.

* * * * *